United States Patent [19]

Brandon et al.

[11] Patent Number: 5,053,327

[45] Date of Patent: Oct. 1, 1991

[54] HIGH AFFINITY MONOCLONAL ANTIBODIES TO BOWMAN-BIRK INHIBITOR AND IMMUNOASSAY METHODS

[75] Inventors: David L. Brandon, Berkeley; Anne H. Bates, Lafayette; Mendel Friedman, Moraga, all of Calif.

[73] Assignee: The United States of America as represented by the Secretary of Agriculture, Washington, D.C.

[21] Appl. No.: 246,842

[22] Filed: Sep. 20, 1988

[51] Int. Cl.[5] ............................................. G01N 33/53
[52] U.S. Cl. .................................... 435/7.92; 435/184; 435/240.27; 435/23; 436/548; 530/808; 530/809
[58] Field of Search ........... 435/7, 184, 172.2, 240.27, 435/23; 436/548, 533, 86; 530/808, 809; 426/231

[56] References Cited

U.S. PATENT DOCUMENTS 4,196,265   4/1980   Koprowski et al. .............. 424/85 X
4,271,145   6/1981   Wands ................................... 424/85

OTHER PUBLICATIONS

Paul, W. E., *Fundamental Immunology*, "Antigen-Antibody Interaction", Ch. 23, pp. 595-605, Raven Press, N.Y., 1984.
Burdon, et al., *Monoclonal Antibody Technology*, vol. 13, Ch. 10, pp. 208-211, Elsevier, Amsterdam, 1986.
E. Offir, M. Trop, and Y. Birk, "Studies of the Antigenicity of Trypsin Inhibitors from Soybeans and Lima Beans", (Abstract), *Israel Journal of Chemistry*, 9: 17BC-18BC (1971).
Y. Birk, "Structure-Activity Relationships of Several Trypsin and Chymotrypsin Inhibitors from Legume Seeds", *Bayer Symposium V Proteinase Inhibitors*, Springer-Verlag, Berlin, pp. 355-361 (1974).
D. L.-R. Hwang, K.-T. D. Lin, W.-K. Yang, and D. E. Foard, "Purification, Partial Characterization, and Immunological Relationships of Multiple Low Molecular Weight Protease Inhibitors of Soybean", *Biochimica et Biophysica Acta* 495: 369-382 (1977).
D. L. Hwang, W.-K. Yang, and D. E. Foard, "Rapid Release of Protease Inhibitors from Soybeans", *Plant Physiology* 61: 30-34 (1978).
A. L. Tan-Wilson and K. A. Wilson, "Nature of Proteinase Inhibitors Released from Soybeans During Inhibition and Germination", *Phytochemistry* 21: 1547-1551 (1982).
A. L. Tan-Wilson, B. R. Rightmire, and K. A. Wilson, "Different Rates of Metabolism of Soybean Proteinase Inhibitors During Germination", *Plant Physiology* 70: 493-497 (1982).
A. L. Tan-Wilson et al., "Bowman-Birk Proteinase Isoinhibitor Complements of Soybean Strains", *Journal of Agricultural and Food Chemistry* 33: 389-393 (1985).
S. Odani and T. Ikenaka, "Studies on Soybean Trysin Inhibitors, VIII Disulfide Bridges in Soybean Bow- (List continued on next page.)

*Primary Examiner*—Christine Nucker
*Assistant Examiner*—Laurie Scheiner
*Attorney, Agent, or Firm*—M. Howard Silverstein; John D. Fado; Margaret A. Connor

[57] ABSTRACT

Hybrid cell lines (hybridomas) which produce and secrete high affinity monoclonal antibodies specific for Bowman-Birk inhibitor (BBI) are described. High affinity antibodies to BBI are described that have one or more of the following additional characteristics: (1) they are specific to the active form of BBI, that is, they react and bind with undenatured BBI, but do not bind with BBI which has been denatured by heat or disulfide exchange; (2) they do not react and bind with KTI; (3) they distinguish classical BBI from other BBI's including lima bean protease inhibitor; and (4) they bind BBI-protease complex, e.g., BBI-chymotrypsin. Immunoassay methods using the monoclonal antibodies to analyze BBI specifically in plant, animal or human tissue or fluid or foodstuffs and techniques for immunoaffinity binding of BBI are described.

17 Claims, 4 Drawing Sheets

OTHER PUBLICATIONS man-Birk Proteinase Inhibitors", *Journal of Biochemistry* 74: 697–715 (1973).

G. Kohler and C. Milstein, "Continuous Cultures of Fused Cells Secreting Antibody of Predefined Specificity", *Nature* 256: 495–497 (1975).

G. Kohler and C. Milstein, "Derivation of Specific Antibody-Producing Tissue Culture and Tumor Lines by Cell Fusion", *European Journal of Immunology* 6: 511–519 (1976).

P. Herion, D. Sieberdt, M. Francotte, J. Urbain, and A. Bollen, "Monoclonal Antibodies Against Plasma Protease Inhibitors: II. Production and Characterization of 25 Monoclonal Antibodies Against Human α-Antitrypsin. Correlation Between Antigenic Structure and Functional Sites", [1]Bioscience Reports 4:139–148 (198).

D. L. Brandon and M. Friedman, "Food Processing to Reduce Protein Allerginicity", (Abstract), 6th International Congress of Immunology, Toronto, Canada, Jul. 6–11 (1986).

D. L. Brandon, S. Hague, and M. Friedman, "Antigenicity of Native and Modified Kunitz Soybean Trypsin Inhibitors", in *Nutritional and Toxicological Significance of Enzyme Inhibitors in Foods*, Ed. M. Friedman, Plenum Press, New York, pp. 449–467 (1986).

D. L. Brandon, S. Hague, and M. Friedman, "Interaction of Monoclonal Antibodies with Soybean Trypsin Inhibitors", *Journal of Agricultural and Food Chemistry*, 35: 195–200 (1987).

HIGH AFFINITY MONOCLONAL ANTIBODIES TO BOWMAN-BIRK INHIBITOR AND IMMUNOASSAY METHODS

BACKGROUND OF THE INVENTION

1. Field of the Invention

The invention relates to and has among its objects the provision of hybridomas that produce and secrete monoclonal antibodies which have high affinity for Bowman-Birk inhibitor, immunoassay methods for the determination of Bowman-Birk inhibitor utilizing the monoclonal antibodies, and immunoaffinity techniques for attaching Bowman-Birk inhibitor to a solid phase.

2. Description of the Art

The protein of legumes, especially soybeans (*Glycine max*), is widely used in human foods. Soy protein is used in a variety of forms including infant formulas, tofu, soy protein isolates, soy flour, textured soy fibers, and soy sauce. Soybean protein products, properly processed, serve as an excellent source of low cost, high quality protein for human needs. Soybeans are even more widely used as a component of animal feeds and are a major export commodity.

Protease inhibitors occur widely in the legume family, comprising 5 to 10% of the storage proteins of the seed. Bowman-Birk inhibitor (BBI) encompasses a class of low molecular weight, double-headed inhibitors (that is, they have two reactive sites which bind to and inhibit proteases). BBI's are products of a group of similar genes and some are also proteolytically modified. In the soybean, the two principal protease inhibitors are the Kunitz trypsin inhibitor (KTI) and the classical Bowman-Birk inhibitor, which inhibits both trypsin and chymotrypsin. Recent evidence suggests that dietary protease inhibitors such as BBI may have a beneficial anticarcinogenic effect through their interaction with a cellular serine protease (J. Yavelow et al., *Cancer Research (Suppl.)* 43: 2454s–2459s (1983); J. Yavelow et al., *Proceedings of the National Academy of Sciences USA* 82: 5395–5399 (1985)). On the other hand, animal studies suggest that active (undenatured) protease inhibitors may be toxic to humans, and may adversely affect nutritional quality. Because protease inhibitors have both beneficial and adverse effects, a need exists to determine the amount and nature of active protease inhibitors present in foods and animal feeds, and determine the balance in food which will result in optimum benefit. In addition, methods for measuring protease inhibitors in plant tissues are needed for evaluating the results of breeding and recombinant DNA studies.

One method to minimize the adverse effects of protease inhibitors in foods is to reduce the amount of active inhibitor. Approaches to reduction of active protease inhibitor content are physical and chemical treatment of soy products and genetic alteration of the soybean crop. Although the protease inhibitor activity is largely inactivated by denaturation through conventionally applied heat treatments of soy flour, 10 to 15% residual activity remains (J. J. Rackis et al., in M. Friedman (ed.) *Nutritional and Toxicological Significance of Enzyme Inhibitors in Foods,* 299–347, Plenum Press, New York (1986)). The problems with this approach are that the nature of the residual activity is difficult to characterize, and the process is costly in energy usage. Genetic modification of the soybean plant to develop varieties with low protease inhibitor content has inherent limitations. Desirable nutritional value and potential anticarcinogenic activity may be lost concomitant with the reduction of protease inhibitor content. Cross-pollination of the genetic variant by a wild-type cultivar could result in reexpression of protease inhibitor genes. In addition, some protease inhibitors may function to prevent predation of the crops by insects, so that some protease inhibitory activities may be important for the agronomic value of soybean cultivars. With either genetic or physicochemical approaches to the reduction of protease inhibitor activity, the ability to measure low levels of protease inhibitors in soybean tissues and derived food products is essential. Since the effects of plant-derived protease inhibitors are of increasing importance in human and animal nutrition, food safety, and plant genetics, it is important to establish the exact protease inhibitor composition of a sample. What is needed is an assay for BBI which has the following characteristics: (1) it is sufficiently sensitive and accurate to measure the low levels of BBI that are present in processed foods, (2) it can differentiate between active BBI and denatured BBI in processed samples, (3) it can differentiate BBI from KTI, and optionally (4) it can differentiate an individual BBI from other BBI's.

Current assay techniques are not capable of providing this information. With regard to enzyme assays, because both BBI and KTI exist as several isoforms, which are derived from different genes or are produced by proteolysis, it is impossible to establish the exact protease inhibitor composition of a sample through enzymatic assay. Moreover, enzyme assays often give inaccurate results with processed samples having low residual activity as found in commercial foods due to inhibition of enzymatic activity or interference by nonprotein components. Further, enzymatic assays do not differentiate among the various specific and nonspecific inhibitors present.

Although polyclonal antibodies which bind BBI have been reported, these molecules appear to have low antigenicity. To overcome this problem, BBI cross-linked with glutaraldehyde was used to elicit an immune response. However, sensitive immunoassay methods, useful to measure low levels of BBI that are present in seeds, tissues, or complex samples including processed foods or feed could not be carried out using the prior art antibodies. With regard to antibodies to BBI that have been reported, a first group of researchers, E. Offir et al., *Israel Journal of Chemistry* 9: 17BC–18BC (1971) and Y. Birk, *Bayer Symposium V "Proteinase Inhibitors,"* Spring-Verlag, Berlin, pp. 355–361 (1974), described antibodies to classical BBI which cross-reacted with lima bean inhibitor (LBI), (an inhibitor which is about 90% homologous to classical BBI) but had only slight binding to KTI. A second group, D. L. -R. Hwang et al., *Biochimica et Biophysica Acta* 495: 369–382 (1977) and D. L. Hwang et al., *Plant Physiology* 61: 30–34 (1978), described antibodies elicited with glutaraldehyde-treated BBI, a treatment which appeared necessary to elicit antibodies suitable for radioimmunoassay (RIA) of BBI. This group set up RIA's for BBI, using BBI iodinated with $^{125}$I as labeled ligand. The RIA relied on precipitation of the BBI-antibody complexes, did not use solid-phase methods, and did not address the selectivity for active BBI as opposed to denatured BBI. Most strikingly, the RIA was insensitive—0.1 mg BBI/ml was the approximate limit of sensitivity. The usefulness of such an assay would be limited to very concentrated solutions rich in BBI. The assay would not be useful for complex food samples, for example. The antibodies were used to distinguish classical BBI from other protease inhibitors in soybean extracts and to monitor the release of inhibitors upon germination of soybeans. A third group of researchers, A. L. Tan-Wilson and K. A. Wilson, *Phytochemistry* 21: 1547–1551 (1982); A. L. Tan-Wilson et al., *Plant Physiology* 70: 493–497 (1982), and A. L. Tan-Wilson, et al., *Journal of Agricultural and Food Chemistry* 33: 389–393 (1985) also used antibodies elicited with glutaraldehyde-treated BBI. They noted changes in antiserum specificity during the course of immunization of the rabbits, and used a precipitation method—radial immundiffusion—to measure changes in BBI during germination of soybeans and the concentration of BBI in different tissues of soybean. Only unlabeled BBI was used in these assays, and specificity for active BBI as opposed to denatured BBI or LBI, or applicability of methods to food samples was not addressed.

The production of monoclonal antibodies by fusion of spleen cells and myeloma cells has been described previously by G. Kohler and C. Milstein, *Nature* 256: 495–497 (1975) and many other investigators. Monoclonal antibodies against protease inhibitors from animal sources are known (See P. Herion et al., *Bioscience Reports* 4: 139–148 (1984)). Monoclonal antibodies to the plant protease inhibitor KTI, a single-headed inhibitor of trypsin (molecular weight about 20,000), have been described and applied to the measurement of KTI in soy samples (D. L. Brandon and M. Friedman, Abstract, 6th International Congress of Immunology, Toronto, Canada, July 6–11, 1986; D. L. Brandon et al., in M. Friedman (ed.) *Nutritional and Toxicological Significance of Enzyme Inhibitors in Foods,* 449–467, Plenum Press, New York (1986), and D. L. Brandon et al., *Journal of Agricultural and Food Chemistry* 35: 195–200 (1987)).

As stated above, previous investigators treated BBI with the crosslinking agent glutaraldehyde in order to render it sufficiently immunogenic. It was therefore unknown whether the appropriate monoclonal antibody specificity could be elicited with unmodified, low molecular weight (about 8000) BBI. It was also unknown whether antibodies could be generated with high affinity to BBI to provide for detection of low levels of BBI present in seeds, tissues, processed foods and the like. Further, it was unknown whether active BBI could be distinguished from BBI denatured by heat or chemical treatment or whether sufficiently specific antibodies could be prepared which could differentiate among classical BBI, and other BBI's such as LBI. It was also unknown whether immunoassays would yield linear responses useful in detecting low levels of BBI in samples containing multiple protease inhibitors and containing phytate, fat, fiber, and other potentially interfering substances. Further, it was unknown whether BBI could be measured in the presence of BBI-binding proteins such as chymotrypsin or other proteins which might be found in products and tissues derived from the soybean. The identification of BBI as part of a complex is important because it would allow quantitation under conditions where enzymatic assays would be inaccurate or impossible. Quantitation of complexes containing BBI in animal and human tissues is important in studies of allergenicity of soy protein, in nutritional and toxicological studies, and in pharmacological investigations of anti-carcinogenic effects.

Various immunoassays, including enzyme-linked immunosorbent assay (ELISA) methods have been used for quantitation of protease inhibitors like KTI (Brandon et al., 1987, supra). However, BBI has some features which made the practicality of monoclonal antibody-based immunochemical methods uncertain. As discussed above, BBI is a small molecule of low antigenicity in rabbits. It could not therefore be predicted that an immune response could be generated in other species, such as the mouse. Further, it could not be predicted that BBI could be attached to another molecule for use as a labeled ligand with retention of its antigenic structure. Retention of structure under these circumstances is necessary for synthesis of nonradioactive derivatives with long shelf life suitable for commercially useful assay kits. Retention of antigenic structure is essential to achieve the specificity and sensitivity required of the immunoassays. Further, it is known that some proteins undergo structural changes which affect their antigenicity when adsorbed onto plastic assay plates (S. E. Dierks at al., *Molecular Immunology* 23: 403–411 (1986)), so it could not be predicted that the antigenic sites of BBI and its complexes with proteases would be readily measurable utilizing solid-phase assay formats.

Retention of antigenic structure would not be sufficient to permit a solid-phase assay. Binding by a small molecule like BBI to the solid phase could leave the antigenic site or sites sterically hindered and unable to bind antibody. Therefore, it could not have been predicted that BBI could be coated on a solid phase for a practical ELISA method. In addition, it was unknown whether a monoclonal antibody with the appropriate specificity and affinity for BBI would also release BBI from the antibody complex under mild conditions to permit a practical affinity chromatography procedure. If BBI could not be released under mild conditions, it would not retain its native configuration, and the method might be useless for purification of BBI or for specific targeting of BBI to a particular site. Further, it was not expect that BBI could be bound by specific monoclonal antibodies and fully retain its ability to interact with a protease, for example, chymotrypsin. The antibody could cause a change in the shape of the chymotrypsin-reactive site or could sterically hinder this site. The ability of an antibody to bind without altering or hindering the chymotrypsin-reactive site would permit targeting BBI to a particular tumor cell, for example, where it could react with a chymotrypsin-like site important in carcinogenesis.

SUMMARY OF THE INVENTION

The invention comprises hybrid cell lines (hybridomas) which produce and secrete monoclonal antibodies having high affinity for Bowman-Birk inhibitor. The high affinity of monoclonal antibodies described herein can produce an assay sensitivity 100-fold greater than polyclonal antibodies of the prior art (analyzed by inhibition enzyme-linked immunosorbent assay (ELISA)).

We have found that high affinity antibodies can be obtained by immunization with BBI that has not first been treated with the crosslinking agent glutaraldehyde. It was surprising that the appropriate monoclonal antibody specificity could be elicited with unmodified BBI which is a low molecular weight protein because, as discussed above, previous workers used glutaraldehyde-treated BBI for immunizations and stated that uncrosslinked BBI is not sufficiently immunogenic to elicit suitable antisera. Our results demonstrate for the first time that unmodified BBI is immunogenic to mice, elicits an antibody response, and activates sufficient numbers of spleen cells to permit hybridoma formation.

Another aspect of the invention is the provision of high affinity monoclonal antibodies to BBI which have one or more of the following additional characteristics: (1) they are specific to the active form of BBI, that is, they react and bind with undenatured BBI, but do not bind with BBI which has been denatured by heat or disulfide exchange; (2) they do not react and bind with KTI; (3) they distinguish classical BBI from other BBI's including LBI; and (4) they bind BBI-protease complex, e.g., BBI-chymotrypsin. High affinity monoclonal antibodies to BBI having some or all of the aforementioned characteristics are encompassed by the invention.

Another aspect of the invention is the provision of screening methods to obtain high affinity monoclonal antibodies to BBI having the aforementioned characteristics.

Still another aspect of the invention is the provision of immunoassay methods for the determination of BBI which utilize the monoclonal antibodies described above. Because the assays utilize high affinity monoclonal antibodies which can detect BBI at very low levels, and optionally be specific for active BBI, or an individual BBI, or not cross react with KTI, the invention fulfills the important needs described above.

Another important point is that assays using monoclonal antibodies of the invention are capable of detecting low levels of BBI in samples containing multiple protease inhibitors and in the presence of polyphenols, phytate, fiber, and other substances which interfere with existing assays.

Another aspect of this invention is to provide antibodies and immunochemical methods for binding, measuring, targeting of BBI, even when the molecule is bound to chymotrypsin or a similar enzyme. The ability to detect BBI while it is bound to other proteins is a unique attribute of the methods described herein, and facilitates quantitation of BBI in complex mixtures such as foods, samples derived from plant tissues, or in tissues or fluids derived from humans or animals. In addition, the methods can be used to target BBI to specific sites. These sites could be part of a matrix used for chromatography or they could be sites on tumor cells, for example. Classical BBI could be targeted to cellular sites, without interference with its chymotrypsin-reactive site, by use of these antibodies. Such targeting would exploit the anti-cancer effects attributed to the chymotrypsin-reactive site.

Another aspect of the invention is to provide kits for the assay of BBI's.

Another aspect of the invention is to provide kits for the analysis of soybean protease inhibitors by using the monoclonal antibodies of the invention together with monoclonal antibodies specific for KTI.

Another aspect of the invention is to provide a method for purification of BBI from crude extracts of plants using the monoclonal antibodies of the invention.

In summary, this invention provides high affinity monoclonal antibodies to BBI as a means for: (1) accurately and rapidly measuring low levels of BBI such as are present in processed foods; (2) specifically measuring active BBI in the presence of denatured forms; this would allow for monitoring active BBI in processes used to inactivate protease inhibitor activity so as to minimize damage to a food and minimize energy requirements of the process; (3) distinguishing between the principal protease inhibitors found in soybeans which cannot be distinguished by other methods; (4) screening soybean seeds in plant breeding studies; (5) screening new plant varieties, plant tissue cultures, and microbes for the expression of genes coding for BBI; (6) accurately determining the levels and sites of localization of BBI in tissues and fluids of animals and humans; (7) attaching BBI specifically to preselected sites; and (8) purifying BBI.

In accordance with this discovery, it is an object of the invention to provide monoclonal antibodies with a high affinity for BBI and methods of using the antibodies for facile and accurate measurement of BBI.

Another object of the invention is to provide immunoassay methods for measurement of BBI in very low levels in plant tissues and processed foods.

It is still a further object to provide a method to study the expression and regulation of plant protease inhibitor genes.

Still another object of the invention is to provide kits useful for the assay of BBI.

It is a further object of the invention to provide a method to attach BBI to a specific site without impairing its reactivity with a protease.

A further object of the invention is to provide a method for purifying BBI.

Other objects and advantages of this invention will become readily apparent from the ensuing description.

DETAILED DESCRIPTION OF THE INVENTION

Definitions.

Bowman-Birk inhibitor is defined as any one member of a family of low molecular weight protease inhibitors naturally occurring in the Leguminosae, with molecular weight about 8000 (7800–8800) and a single polypeptide chain of about 70 to 80 amino acid residues, including 7 cystines. Bowman-Birk inhibitors are double headed, i.e., have two reactive (protease-binding) sites and can bind simultaneously with two protease molecules. The specificity of the reactive sites for proteases (e.g., trypsin, chymotrypsin, elastase, etc.) depends on the specific inhibitor. Variants and synthetic products with homologous structure and protease inhibitory activity are included.

The classical BBI double-headed inhibitor of chymotrypsin and trypsin obtained from soybeans has a molecular weight of 7995 (Y. Birk, 1974, supra) by amino acid analysis. The amino acid composition and sequence of this molecule are known (S. Odani and T. Ikenaka, *Journal of Biochemistry* 74:697–715, (1973)) and consist of 71 amino acid residues. Minor variants and synthetic products based on the same structure are included in the definition.

Lima bean inhibitor is defined as BBI from lima beans and is as much as 90% homologous in amino acid sequence with classical BBI.

Denatured BBI is defined as BBI which has been treated to cause at least 90% loss of protease-inhibiting activities. Exemplary of such treatments are: steam treatment at 121° C. for 20 minutes; treatment at 85° C. or higher for 1 hour with a disulfide modifying agent, that is, a compound which induces breakage and/or rearrangement of the disulfide bonds of undenatured BBI. Such agents include N-acetylcysteine (NAC) and sodium sulfite. Extrapolations from these conditions to cause loss of chymotrypsin- and trypsin-inhibiting activities can readily be determined by test runs.

Active BBI is defined as BBI which has not been denatured as described above.

High affinity monoclonal antibodies to BBI are defined as monoclonal antibodies which bind BBI with an affinity constant of at least $8 \times 10^7 M.^{-1}$ Affinity constant is defined as the reciprocal of the concentration of BBI which results in half-maximal binding of antibody in inhibition ELISA or equivalent affinity determined by other techniques.

Methods.

The method of preparing the hybridomas comprises the following steps:

Immunization. The immunizing preparation consists of a protein mixture including BBI. It may contain other proteins, or it may be a homogeneous, pure preparation of a single Bowman-Birk inhibitor or could be used without treatment. The preferred immunization preparation is an untreated, purified preparation of a single BBI. However, optionally, the pure protein or protein mixture can be treated (such as by crosslinking or attachment to an immunogenic carrier).

As discussed above, polyclonal antibodies reported by previous workers were prepared using glutaraldehyde-treated BBI for immunizations. BBI's are small molecules of low antigenicity in rabbits. It could not, therefore, be predicted that an immune response could be generated in other species such as the mouse. Our invention is the first report that uncrosslinked BBI is immunogenic in mice, elicits an antibody response, and activates sufficient spleen cells to permit hybridoma formation.

The preparation of hybridoma cell lines can be done by techniques which are well known to those who are skilled in the art. (See, for example, G. Kohler and C. Milstein, 1975, supra; *European Journal of Immunology* 6: 511–519 (1976); Koprowski et al., U.S. Pat. No. 4,196,265, and Wands, U.S. Pat. No. 4,271,145, all of which are herein incorporated by reference.)

The choice of animal for immunization is limited by the availability of the fusion partner—the permanent plasmacytoma cell line, and mouse, rat, and human hybridomas have been prepared by many investigators. Mice are preferred because of ease of handling.

Inoculations of the animal can be by various routes. A series of inoculations, generally at three week intervals, with an immunogen such as a BBI protein preparation emulsified in complete Freund's adjuvant, elicits good antibody response after two to three inoculations. A suggested inoculum is 10–100 µg of BBI emulsified in complete Freund's adjuvant. Other routes and immunization schedules and other adjuvants or no adjuvant are alternatives. In addition, the generation of an immune response can be performed in vitro.

The choice of cell line as fusion partner can influence the results, including frequency of cell fusions and growth characteristics of the resulting hybridoma. However, many cell lines are widely available. Exemplary of two cell lines are P3-NS1-1-Ag4-1 and the closely related P3X63-Ag8.653.

Production of Hybrid Cells. Cell fusion techniques, selection procedures, and methods for growth of hybridomas are known to those skilled in the art. In one effective cell fusion procedure, poly(ethylene glycol) (PEG) is used in the fusion step, and hypoxanthine-aminopterin-thymidine (HAT) is used in the selective medium.

Analysis of Hybridomas. The growing colonies are tested for the presence of antibodies that recognize the antigenic determinants of BBI. Detection of hybridoma antibodies can be performed with a variety of assays. We have found that one way is to attach BBI to the surface of assay wells in a multiwell microtitration plate made of polystyrene and widely available commercially. Standard assay methodology and widely used commercial reagents, such as rabbit anti-mouse immunoglobulin G (IgG) antibodies attached to horseradish peroxidase (HRP), can be used to reveal the presence of antibodies in the culture supernatants. The ability of the antibody to bind selectively to an individual BBI can be tested at this stage, or after cloning. It is preferred to confirm the specificity of the BBI-antibody interaction by using inhibition ELISA, or equivalent analytical method.

Cloning of Hybridomas. Cloning of hybridomas which are positive for desired antibody production can be carried out as soon as they are detected by any method known to the art. In the preferred embodiment, cloning is accomplished by limiting dilution in liquid medium. The cloning procedure can be repeated to increase the probability of clonality. Antibody-secreting hybridomas can be grown in a variety of vessels, in devices such as hollow fibers, or within a host animal.

Systematic Screening of Clones. To obtain the monoclonal antibodies of the invention, systematic screening is carried out as follows:

Preliminary Screening. Supernatant culture fluid from the cloned hybridomas of interest is optionally submitted to a preliminary screening to confirm the presence of antibodies that recognize the antigenic determinants of BBI. We have found that the direct binding assay (or titration), using plastic assay wells coated with BBI, is a convenient and efficient technique for the preliminary screening step.

Screening for High Affinity Antibodies to BBI. Supernatant culture fluid from the cloned hybridomas of interest is screened to select antibodies having a high affinity for BBI as defined above. Affinity can be measured by any technique known in the art for example, inhibition ELISA, equilibrium dialysis using labeled BBI, or RIA. Where the contemplated use of the antibody is in an ELISA assay, inhibition ELISA is the screening technique of choice. Inhibition ELISA is conducted at a final antibody concentration (i.e., dilution from tissue culture supernatant) to give 50 to 100% of maximal binding to a BBI-coated assay well. Antibody is mixed with a range of concentrations of BBI, incubated, and applied to the assay plate. The plate is then incubated, washed, and developed as for the direct binding assay. Antibodies are selected which are at least 90% inhibited from binding to the solid phase by BBI at less than 100 ng/ml.

It was unexpected that antibodies having such high affinity to BBI would be generated. Although polyclonal antibodies to BBI have been reported, the antibodies of the invention can produce an assay sensitivity (analyzed by ELISA) 100-fold greater than the polyclonal antibodies of the prior art.

Further, it could not be predicted that monoclonal antibodies to BBI could be useful in immunoassays such as the direct binding assay. It is known that some proteins undergo structural changes which affect their antigenicity when adsorbed onto plastic assay plates, so it could not be predicted that the antigenic sites of BBI would be readily measurable using solid-phase assay formats. It was not known whether adsorption of a small protein like BBI to the solid phase would leave the antigenic site or sites sterically hindered and unable to bind antibody. Therefore, it could not have been predicted that BBI could be coated on a solid phase for a practical ELISA method.

Screening for Antibodies which are Specific for Individual BBI's. Screening for antibodies which are specific for one or more individual BBI's is conducted by screening the high affinity antibodies to BBI obtained above for those which do not bind to other BBI's. This can be carried out by any technique known in the art, for example, inhibition ELISA and the like. It is preferred to test for binding with a direct binding assay, using the other BBI's coated on a solid phase. Antibodies are selected which show no binding to the other BBI's. Since antibodies with such specificity are rare, and the direct binding assay provides a very rigorous test of specificity, some desired antibodies will only be screened properly by inhibition ELISA. This screening is conducted with the individual BBI's coated on the solid phase. Antibody is used at a concentration giving 50 to 100% of maximal binding to the individual BBI, and is mixed with other BBI's at a range of concentrations from 10 to 10,000 ng/ml. Antibodies are selected which show no inhibition by the other BBI's up to at least 1000 ng/ml and which show at least 100-fold increased binding to the individual BBI compared to the other BBI's.

Screening for Antibodies Which Do Not Bind to Denatured BBI. Screening for high affinity antibodies to BBI which have the additional characteristic that they do not react and bind with denatured BBI is conducted by any technique known in the art, for example, inhibition ELISA. BBI may be denatured using the several conditions described above.

Screening for Antibodies That Do Not Bind to KTI. Screening for antibodies which do not bind to KTI is conducted by testing the high affinity antibodies to BBI obtained above for those which do not bind to KTI. This can be carried out by any technique known in the art, for example, inhibition ELISA and the like, as in the paragraph above.

Screening for Antibodies Which Can Bind BBI-Chymotrypsin Complex. Screening for antibodies which can bind BBI which is in a complex with chymotrypsin is conducted as follows. This procedure is applicable to inhibitors with at least one chymotrypsin-reactive site, for example, classical BBI. Complexes of BBI with chymotrypsin are formed by mixing BBI with chymotrypsin in a molar ratio of 1:3. After a suitable time, e.g., about 10 minutes, phenylmethylsulfonyl fluoride is added to inhibit excess chymotrypsin. BBI complexes and a control sample of BBI are diluted serially for inhibition ELISA using the appropriate concentration of monoclonal antibody, incubated for about 30 minutes, and applied to BBI-coated assay plates for about 40 minutes. Plates are developed as described above. Antibodies are selected which have identical binding for BBI and BBI complexes with chymotrypsin. This procedure is applicable to screening for antibodies which can bind to other BBI-protease complexes, for example, complexes with trypsin or elastase.

The antibodies of the invention possess several unique features. The monoclonal antibodies of the invention are specific for BBI. They are of high apparent affinity, which makes them suitable for a wide variety of immunoassays. Binding can be achieved in the very low concentration range of 10 to 100 ng/ml, suitable for analysis of residual levels of BBI in complex, processed foods. Antibodies can be obtained which do not bind to KTI and do not bind to BBI which has been denatured by heat or disulfide exchange. No equivalent specificity or sensitivity of analytical immunochemical methods has yet been reported in the literature. Sensitivity of immunoassay is at least 100-fold greater than reported by Hwang et al., 1977, supra.

The antibodies can bind to BBI which has been labeled with a molecule such as biotin or HRP. Retention of antigenicity by labeled BBI with respect to the monoclonal antibodies of the invention is a unique feature, which would enable a variety of convenient labeled forms of BBI to be used in immunochemical methods. The antibodies of the invention can be covalently attached to a solid phase such as agarose with retention of activity. BBI bound to the antibodies of the invention can be released by mild acid treatment. This treatment does not denature the antibodies, permitting, for example, multiple uses of affinity chromatographic matrices containing the antibodies.

The above features are surprising because it could not be predicted that the low molecular weight BBI would elicit a sufficient antibody response to permit the isolation of monoclonal antibodies specific for BBI and with sufficient affinity to permit sensitive immunochemical methods. It could not be predicted that monoclonal antibodies could be prepared which would not bind to BBI denatured by heat or disulfide exchange. Further, it was not expected that monoclonal antibodies to BBI would yield immunoassays which agreed closely with enzymatic assays for samples of BBI with low residual activities following heat and chemical treatments. It was unknown whether high affinity antibodies specific for BBI could bind to BBI in the presence of chymotrypsin. In addition, it was unpredictable that monoclonal antibodies to BBI would have appropriate affinity and stability to permit immunoaffinity techniques. It was also unknown whether BBI could be attached to another molecule to make a labeled ligand with retention of its antigenicity with respect to highly specific, high affinity monoclonal antibodies.

Hybridomas which produce and secrete high affinity monoclonal antibodies to BBI were prepared as described above. Representative of these is clone 238 which produces and secretes antibodies that have high affinity to soybean BBI and do not crossreact with KTI, LBI, or denatured BBI. Clone 238 has been deposited in the American Type Culture Collection, Rockville, Md., with the accession number ATCC HB 9657.

Uses of Monoclonal Antibodies of the Invention.

Measurement of BBI. The measurement of BBI is carried out using the monoclonal antibodies of the invention. The preferred method is use of ELISA.

Inhibition ELISA. In this assay, a sample to be analyzed is incubated with monoclonal antibody specific for BBI. Portions of this mixture are transferred to any solid phase, such as wells of an assay plate, a bead, or a solid-state electronic device, coated with native BBI. After an incubation (one hour preferred), the solid phase is drained, washed, and rinsed, and bound antibody is detected. The preferred method of detection on an assay plate or bead is use of an enzyme-labeled second antibody recognizing the monoclonal antibody. HRP and its substrate, 2,2'-azinobis-3-ethylbenthiazolinesulfonic acid (ABTS), are preferred reagents for labeling and measuring bound antibodies. The immunoassay can be performed using other labels, such as radiolabels or chromophores, or with directly labeled monoclonal antibody. If an electronic device is used as solid phase, an appropriate electronic detector is used.

A standard curve relating the amount of bound monoclonal antibody to BBI concentration is constructed from assays using authentic BBI. The concentration of BBI in the sample is determined by reference to the standard curve.

Competition ELISA. In this variation of the assay, monoclonal antibody specific for BBI is attached to a solid phase, with multiwell plastic microtitration plates the preferred embodiment. Covalent attachment to a surface, bead, solid-state electronic device or relatively nonspecific adsorption to such surfaces may be employed. Sample to be analyzed is mixed with an appropriate amount of labeled BBI, which can be labeled with biotin, HRP, or other labels such as chromophores, radiolabels, paramagnetic labels, and the like. The mixture of labeled BBI and analyte is applied to the solid phase, and after incubation (one hour preferred), the solid phase is drained, washed and rinsed, and bound labeled BBI is determined by a method dependent on the surface and label used. In a preferred embodiment, HRP-labeled BBI is visualized with ABTS as substrate. The amount of BBI in the sample is determined with reference to a standard curve as described above.

Attachment of BBI to a Targeted Site. Monoclonal antibody specific for BBI is specifically attached to the site of interest. This attachment could be covalent (as in Example 3, below), or could be through another antibody molecule binding site, for example. Thus, the monoclonal antibody specific for BBI can be combined with another antibody specific for the site of interest by techniques known to the art. BBI will then be able to bind selectively at the site of interest, and still be able to inhibit proteases.

Characterizing the Trypsin Inhibitory Activity of Soybeans by Distinguishing Between BBI and KTI. An extract of soy protein-containing substance such as a seed or tissue of a soybean plant or a food is prepared by any technique known in the art. BBI is measured in a portion of the extract as described above in "Measurement of BBI," with competition ELISA the preferred embodiment. KTI is measured by any immunoassay known in the art, with the preferred embodiment being competition ELISA using monoclonal antibodies specific for KTI.

Measurement of Active BBI in Processed Foods. BBI is measured as described above in "Measurement of BBI," using monoclonal antibodies of the invention which are specific for active BBI. This is described in detail in Example 2 below.

Measurement of BBI Which Is In a Complex With Protease. BBI which has a reactive site for a protease, e.g., chymotrypsin, can be measured in the presence or absence of the protease by following the procedure described above in "Measurement of BBI," using antibodies of the invention which have been screened for their ability to bind to BBI-protease complex. This is described in detail in Example 1 below.

Applicability of Techniques.

The choice of particular technique and reagents depends on the particular application, since simplicity and cost (among other parameters) vary. But anyone skilled in the art could apply the generalized techniques.

These procedures for analysis of BBI-containing samples can be readily automated, for example by provision of automatic pipeting equipment and automated ELISA reader and computer. The invention can also be adapted to a variety of kits, in which antibody, suitably labeled BBI, or anti-immunoglobulin, substrate, and standards are supplied in separate containers, or, as appropriate, coated on solid phases. The surface could be a plastic assay dish, a bead, or electronic solid-state transducer that would permit on-line monitoring, for example. Reagents may be provided in solid or liquid form. The assay could also be arranged as a qualitative assay—such as might be used in a quality control application. In such a format, the appropriate reagents would be coated on surfaces and supplied in solutions at concentrations which would reveal a positive assay if more than a predetermined minimum of BBI were present in the sample. Such a kit could include materials for assay of KTI and thus comprise a method for determination of both major protease inhibitors of soy.

The sample can consist of any product which may contain BBI, including foods derived from legumes, such as flour, infant formulas, meat products containing soy extenders, or any tissue derived from a plant or organism expressing a gene product similar to BBI. The sample could be a human or animal tissue, for example in determining the fate of BBI in the digestive tract or its presence on a cell surface, within a cell, or as an immune complex.

The ELISA methods could be applied in several ways. (a) Food samples could be analyzed for BBI remaining after thermal treatment or after fractionation of protein isolates. (b) The relatively stable BBI molecule could be used as a marker to detect soy protein as an adulterant in meat products. Such applications would benefit from the added simplicity and speed of assays using labeled BBI. BBI can be labeled with biotin ester or HRP to provide a stable, easily detected ligand in which the BBI antigenicity is retained. (c) In plant genetics, the ELISA could detect the product of the BBI gene or closely related genes. For example, the ELISA could be used to detect levels of BBI in seeds used in breeding studies, where it may be desirable to eliminate BBI activity while retaining the high sulfur content of the BBI polypeptides. Antibodies to BBI might detect altered forms of BBI which have modified reactive sites but similar three-dimensional structures. Cultivars containing such structures could have higher nutritional value than conventional cultivars and would require less thermal processing. (d) It may be useful to detect an altered form of BBI with chymotrypsin inhibitory activity—and thus possible anti-carcinogenicity—but without the trypsin inhibitory activity associated with pancreatic toxicity.

Another application of the monoclonal antibodies to BBI is affinity purification of BBI. In addition, the successful attachment of antibody to agarose demonstrates that antibody-directed targeting of the inhibitor is feasible.

An important potential application of these findings is the targeting of BBI to specific cellular sites. For example, a bispecific antibody—with one site specific for a tumor cell antigen and the other for BBI—would provide a means to deliver BBI to tumor cells. Since tumor cells have surface proteases similar to chymotrypsin which appear to regulate cellular proliferation, the selective, antibody-mediated attachment of BBI to these cells could be an effective cancer treatment.

EXAMPLES

The following examples are intended only to further illustrate the invention and are not intended to limit the scope of the invention which is described by the claims.

EXAMPLE 1

This example describes determination of BBI using inhibition ELISA.

Protease Inhibitors. Kunitz soybean trypsin inhibitor obtained from Sigma Chemical Co., St. Louis, Mo., was characterized by polyacrylamide gel electrophoresis and by inhibition of trypsin as described by M. Friedman et al., *Journal of the Science of Food and Agriculture* 33: 165–172 (1982). KTI was determined to be isoform a. Standard solutions were prepared in phosphate-buffered saline (PBS) (150 mM NaCl, 5 mM sodium phosphate, pH 7.0) or PBS with 0.01% $NaN_3$ (PBS-$N_3$). The solutions were adjusted to 1 mg/ml based on $E_{280}$, 1 mg/ml=1 (B. Kassell, *Methods in Enzymology* 19: 853–862 (1970)) and were stored as aliquots at $-20°$ C. The measurement of trypsin inhibitor activity and definition of TIU were as described by Friedman et al., 1982, supra.

Purified classical BBI was obtained from Y. Birk (Faculty of Agriculture, Hebrew University of Jerusalem, Rehovot, Israel). LBI was obtained from Sigma Chemical Co. The inhibitors were characterized by gel electrophoresis and by inhibition of trypsin and chymotrypsin. Standard solutions were prepared in PBS and their concentration was determined based on $E_{280}$, 1 mg/ml=0.44 (B. Kassell, 1970, supra).

BBI was treated in a variety of ways to simulate conditions which arise during food processing. A sample consisting of 10 ml of 1 mg/ml BBI in 0.5M Tris-Cl buffer, pH 8.5, was heated for 1, 2, or 3 hours without any chemical agent or in the presence of 1 mg/ml NAC or 1 mg/ml sodium sulfite.

Antibody Preparation. Mouse antibodies were elicited in Balb/c mice by two intraperitoneal inoculations at 3-week intervals with 50 $\mu$g of purified BBI emulsified in complete Freund's adjuvant. Antibody production was assessed by ELISA. Monoclonal antibodies were produced as follows. A BBI antibody-producing mouse was inoculated intravenously with 50 $\mu$g of BBI in 0.1 ml of PBS three days prior to cell fusion. Equal numbers of immune spleen cells and myeloma cells (P3X63-Ag8.653, Kearney et al., *Journal of Immunology* 123: 1548–1550 (1979)) were fused by treatment with 50% PEG 1450 (Bethesda Research Laboratories, Bethesda, Md.), and the fusion suspension was dispersed into 96-well tissue culture plates, 0.2 ml/well, at a cell density of $1.5\times10^6$ cells/ml. Hybridomas secreting BBI-specific antibody were identified by ELISA. Fusion culture supernatants were harvested after two weeks growth, diluted (1:10) in PBS or 10 mg/ml bovine serum albumin (BSA) in PBS with 0.05% Tween 20 (BSA-PBS-Tween), and applied to BBI-coated assay wells. Details are given below. Positive cultures were identified (greater than 0.5 absorbance units at 415 nm after 15 minutes). Following transfer and expansion of the cultures, hybridomas were cloned by limiting dilution. Clones were expanded in culture, permitting harvest of supernatant, freezing of cell lines, and preparation of ascites fluid. Monoclonal antibodies were assayed for isotype by a solid-phase assay similar to the direct-binding assay, but using isotype-specific antibodies conjugated to $\beta$-galactosidase (Southern Biotechnology, Birmingham, Ala.). Myeloma proteins (Litton Bionetics, Kensington, Md.) were used to assess the specificity of these antibodies.

Screening for Antibodies which Distinguish between Active and Denatured BBI.

Preparation of BBI-coated Assay Plates. Active BBI (5 $\mu$g/ml, 100 $\mu$l/well) was coated on polystyrene assay plates (Nunc, Roskilde, Denmark). The plates were incubated for 4 to 6 hours and then washed with PBS-Tween and rinsed with distilled water. Remaining sites were blocked by incubating for 1 hour with 200 $\mu$l/well of BSA-PBS-Tween solution. Plates were then re-washed and used immediately or stored for up to 2 weeks in PBS with azide. Assay plates stored longer were less efficient in binding assays.

Direct-binding Assays. Antibody samples to be assayed were serially diluted in BSA-PBS-Tween. The resulting samples (100 $\mu$l/well) were applied to BBI-coated plates, generally in triplicate, and incubated with shaking for 1–2 hours. Plates were emptied, washed, rinsed with distilled water, and drained. Labeled reagent (100 $\mu$l/well of HRP-labeled rabbit anti-mouse IgG) diluted in BSA-PBS-Tween was added, and the plates were incubated for 1 hour with shaking, then washed, rinsed and drained. Next, 100 $\mu$l of substrate (1 mM ABTS, 6.7 mM $H_2O_2$, 60 mM sodium citrate, pH 4.2) was added, and the absorbance at 415 nm was determined on a plate reader (Model 308, Bio-Tek Instruments, Burlington, Vt.). Assays were generally read after 15 minutes or terminated by addition of 100 $\mu$l/well of 10% sodium dodecylsulfate. Antibodies (supernatants from tissue cultures) which gave positive reactions were tested further.

Figure 1:
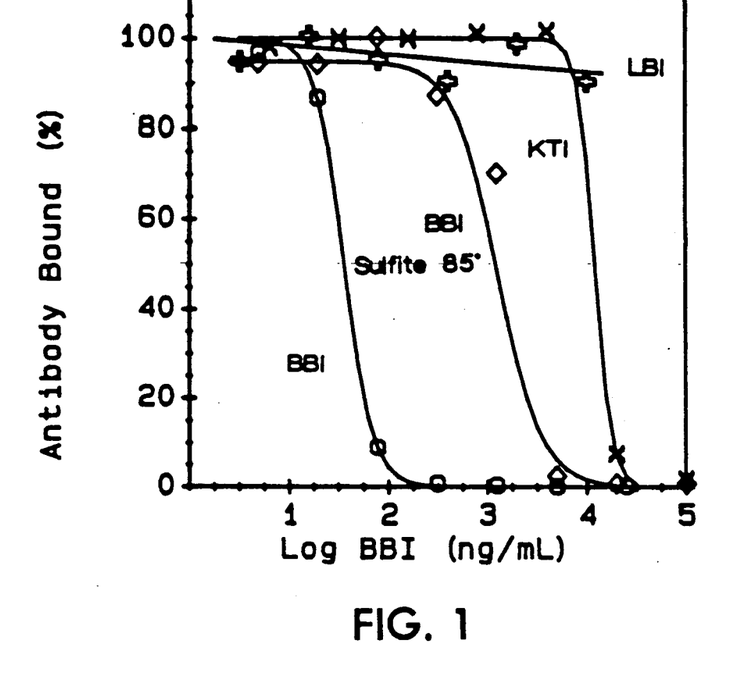
FIG. 1 shows an ELISA standard curve for BBI and assay curves for LBI, KTI, and BBI denatured by treatment with sodium sulfite at 85° C. using a high affinity monoclonal antibody with specificity to active BBI prepared in accordance with the invention.

Inhibition ELISA. Antibody and active (untreated) or treated BBI were mixed and preincubated for 1–2 hours at room temperature prior to assay. Antibodies were used at concentrations falling within the linear range of the direct binding assays above. Aliquots of the preincubation mixtures were assayed as described above for the direct binding assays, using assay plates prepared with classical BBI. FIG. 1 shows that antibody from ATCC HB 9657 is highly specific for untreated BBI, and discriminates against denatured BBI (treated with sodium sulfite at 85° C.). FIG. 1 also shows that there is no detectable crossreactivity with LBI, and less than 0.1% crossreactivity with KTI. The minimal crossreactivity with KTI may well be due to traces of BBI in the sample of KTI. Gel electrophoresis patterns were also consistent with BBI contamination of the KTI sample. The inhibition ELISA curve for the native BBI sample provides a standard curve which can be used to estimate the amount of BBI in test samples.

Antibody Purification. BALB/c mice were injected with 2,6,10,14-tetramethylpentadecane (Aldrich Chemical Co., St. Louis, Mo.) 10 days and 3 days prior to intraperitoneal inoculation with $2 \times 10^6$ viable hybridomas. High-titer ascitic fluid and sera were obtained from four of six treated mice within 3 weeks of inoculation. For use in assays, the IgG fraction was purified from ascitic fluid or by ammonium sulfate precipitation and chromatography on (diethylamino)ethyl cellulose (Whatman, Ltd., Maidstone, U.K.).

Figure 2:
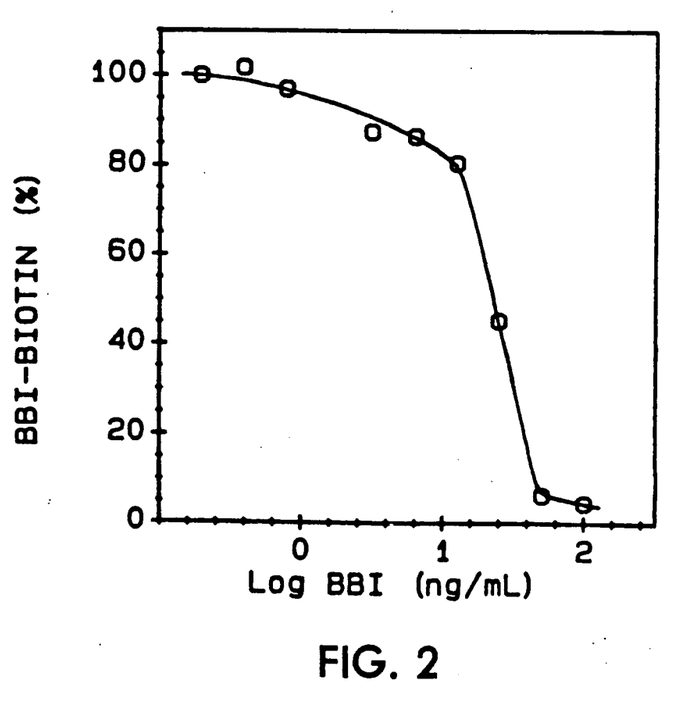
FIG. 2 shows a standard curve for BBI by ELISA using monoclonal antibody of the invention and biotinylated BBI.
Figure 3:
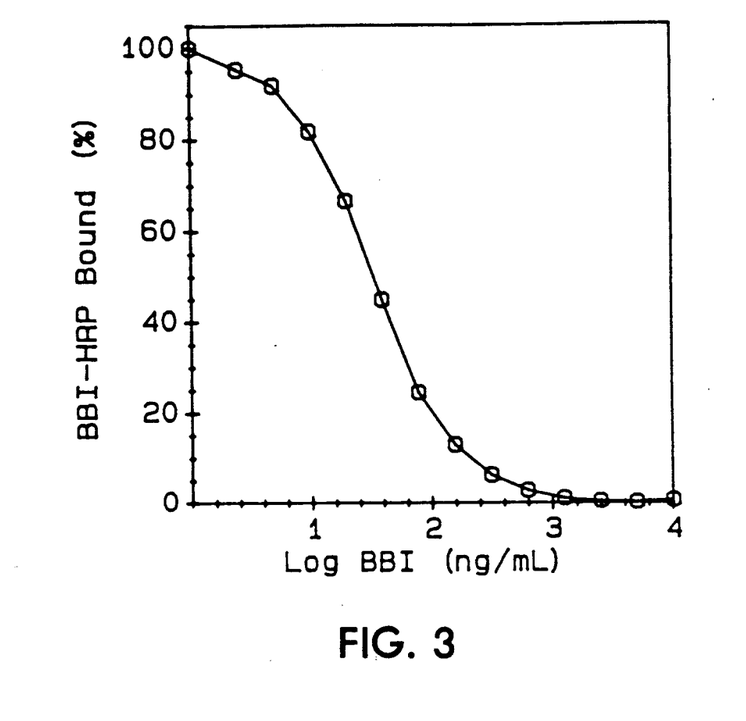
FIG. 3 shows a standard curve for BBI by ELISA using monoclonal antibody of the invention and BBI-HRP.

Competition ELISA. The assay was conducted on assay plates coated with purified IgG anti-BBI (10 μg/ml, 100 μl/ml). Unknowns or standard samples containing BBI were premixed with equal volumes of biotinylated BBI or BBI-HRP and incubated in the assay wells (100 μl/well, 1-2 hours at room temperature with shaking). The binding reaction was complete within one hour, with no change in binding between one and two hours. When biotinylated BBI was used, plates were again washed and rinsed and the assay wells were next incubated with streptavidin-HRP conjugate (Amersham Corp., Arlington Heights, Ill.), 100 μl/well, for 1 hour at room temperature, with shaking. For either label, unbound HRP conjugate was removed by washing and rinsing the plates and the bound HRP was visualized by addition of ABTS substrate solution, 100 μl/well, with incubation for 15 minutes. The absorbance was determined at 415 nm on an ELISA plate reader. FIGS. 2 and 3 illustrate standard curves obtained using this technique.

Figure 4:
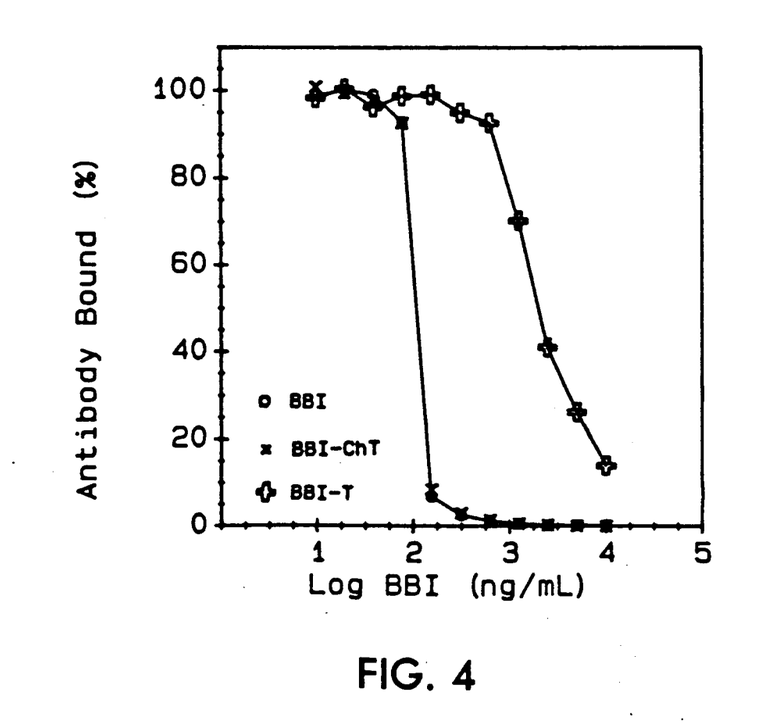
FIG. 4 shows ELISA of BBI, BBI-trypsin, and BBI-chymotrypsin complexes.

Assay of BBI in the presence of trypsin or chymotrypsin. In brief, complexes of BBI with trypsin or chymotrypsin were formed by mixing BBI with trypsin or chymotrypsin in a molar ratio of 1:3. After 10 minutes, excess protease was inhibited by addition of phenylmethylsulfonyl fluoride. BBI complexes or controls were serially diluted with the monoclonal antibody from ATCC HB 9657, incubated for 30 minutes, and applied to BBI-coated assay plates for 40 minutes. The plates were developed as described for inhibition ELISA and resulted in the assay curves plotted in FIG. 4. It is apparent that interaction of BBI with chymotrypsin does not affect its interaction with antibody from ATCC HB 9657. Thus, this antibody could bind BBI, even when BBI was found in a complex with chymotrypsin. Antibody binding to the complex with trypsin was much weaker, suggesting that the epitope overlaps with the trypsin-reactive site.

EXAMPLE 2

Enzymatic assays. Inhibition of trypsin activity was measured at room temperature in 0.4M Tris-Cl, 0.01M $CaCl_2$, pH 8.1, with 1 mM p-toluene-sulfonyl-L-arginine methyl ester as substrate. Bovine trypsin (Sigma Chemical Co.) was present at 0.1 μg/ml and was preincubated with inhibitor for 6 minutes. Absorbance at 247 nm was recorded for 3 minutes for reactions conducted in the presence or absence of inhibitors.

Inhibition of chymotrypsin activity was determined at room temperature in 0.04M Tris-Cl, 0.05M $CaCl_2$, pH 7.8, with 0.5 mM benzoyl-L-tyrosine ethyl ester as substrate. Bovine chymotrypsin (Sigma Chemical Co.) was present at 0.2 μg/ml and was preincubated with inhibitor for 6 minutes. Absorbance at 256 nm was recorded for 3 minutes for reactions conducted in the presence or absence of inhibitors.

Extracts of infant formula powder or soy meal (milled and passed through a 60 mesh sieve) were prepared by suspending 500 mg of nondefatted powder in 15 ml 0.5M Tris-Cl buffer, pH 8.5, and stirring for 1 hour at room temperature. Ten or 20 μl aliquots of the unfiltered suspensions were used for measuring inhibition of trypsin and chymotrypsin.

Comparison of enzymatic assay and ELISA of BBI. BBI was treated at 85° C. in buffer only, or in the presence of NAC or sodium sulfite as described in Example 1. The resulting sample was assayed for trypsin and chymotrypsin inhibition by enzymatic assay as described above and for activity in the inhibition ELISA, using the antibody from ATCC HB 9657. Relative ELISA activity was calculated as follows. The midpoint of the inhibition curve was used to determine the concentration of sample that inhibits antibody binding by 50% ($I_{50}$). The $I_{50}$ was also computed for a control sample. ELISA activity relative to the control was calculated as follows:

Percent activity = $[I_{50}$ (control) $\times 100]/I_{50}$ (sample). The results of this analysis are shown in Table 1.

TABLE 1

| Chemical Agent | Time (hours) | % Activity Remaining | | |
|---|---|---|---|---|
| | | Chymotrypsin Inhibition | Trypsin Inhibition | BBI (ELISA) |
| None | 1 | 75 | 87 | 105 |
| | 2 | 67 | 85 | 100 |
| | 3 | 60 | 69 | 100 |
| NAC | 1 | 8.7 | 15 | 8.7 |
| | 2 | 4.0 | 8.0 | 4.9 |
| | 3 | 2.0 | 4.3 | 2.7 |
| Sodium sulfite | 1 | 6.7 | 13 | 6.9 |
| | 2 | 3.7 | 5.6 | 2.3 |
| | 3 | 1.8 | 3.1 | 1.0 |

It is apparent that there is excellent agreement between the ELISA results and the enzymatic assay, especially in the crucial area of low residual activity. It should also be noted that for samples not treated with a chemical agent, almost all of the 13 to 31% loss of activity, as measured by inhibition of chymotrypsin, was regained when the samples were dialyzed. This apparent reversible denaturation by heat alone may thus account for discrepancies between enzymatic and immunochemical assays for slightly inactivated BBI samples.

Analysis of thermal inactivation of BBI in soybean meal. In these studies, a commercially grown cultivar (Williams) was compared to a low trypsin inhibitor isoline L81-4590 (T. Hymowitz, in *Nutritional and Toxicological Significance of Enzyme Inhibitors in Foods*, Ed. M. Friedman, Plenum Press, New York, 291-298, 1986). Soybeans were ground in a Udy mill, sieved through a No. 60 mesh, and subjected to heat treatment in an autoclave at 121° C. Tris-Cl buffer (0.5M, pH 8.5) was then added (10 ml per 300 mg of soy meal), and the slurry was homogenized with a "Tissuemizer" (Tekmar Co., Cincinnati, Ohio) and stirred for 2 hours at room temperature. Suspensions were assayed for trypsin and chymotrypsin inhibitory activity after a preliminary assay to determine the appropriate dilution in water to achieve 40 to 60% inhibition. Samples were analyzed for BBI by inhibition ELISA using monoclonal antibody from ATCC HB 9657. The results are summarized in Table 2.

TABLE 2

| Soybean Variety | Autoclaving Time (min) | % Activity Remaining | | |
|---|---|---|---|---|
| | | Chymotrypsin Inhibition | Trypsin Inhibition | BBI (ELISA) |
| Williams (Ti$^a$ Ti$^a$) | 10 | 83 | 64 | 84 |
| | 20 | 38 | 26 | 1.9 |
| | 30 | 18 | 17 | 1.4 |
| L81-4590 (ti ti) | 10 | 40 | 83 | 59 |
| | 20 | 10 | 9.3 | 1.7 |
| | 30 | 7.0 | 2.3 | 0.09 |

All the values are stated relative to unheated control samples. These values are as follows. The Williams sample inhibited 150 chymotrypsin units or 4800 trypsin units inhibited per gram and contained 2.9 mg BBI per gram. L81-4590 inhibited 143 chymotrypsin units or 2500 trypsin units per gram and contained 3.0 mg BBI per gram.

The data illustrate that the meal from L81-4590 is indeed lower in trypsin inhibitory activity, consistent with the absence of KTI in this cultivar. In addition, both the chymotrypsin and trypsin inhibitory activities appear more heat-labile in L81-4590, with more than 90% inactivation in 20 min. Significantly, the ELISA analysis indicates that BBI is inactivated more rapidly than the total trypsin or chymotrypsin inhibitory activities. The differences in the ELISA and enzymatic data, most striking in the samples with very low residual activity, reflect contributions of nonprotein inhibitors of the enzymes, and possibly other minor protease inhibitors.

Figure 5:
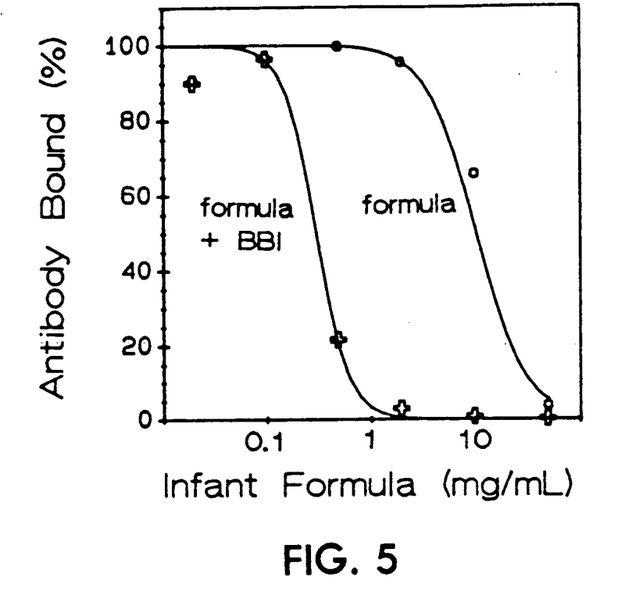
FIG. 5 shows analysis of BBI in soy-based infant formula by ELISA.

Analysis of soy protein infant formula. Isomil infant formula powder (Lot No. RBI 08976, Ross Laboratories, Columbus, Ohio) was purchased at a local store. The formula was reconstituted and analyzed by inhibition ELISA, with or without the addition of a "spike" of authentic BBI. FIG. 5 illustrates inhibition ELISA curves for spiked and unspiked samples. Three analyses yielded the value of 7.4±0.5 µg BBI/gram protein.

EXAMPLE 3

Preparation of antibody-agarose affinity support. One gram of cyanogen bromide-activated agarose (Sepharose 4B, Pharmacia, Inc., Piscataway, N.J.) was washed and swollen in 1 mM HCl. Monoclonal antibody from ATCC HB 9657 (19 mg in 6 ml of 0.1M NaHCO$_3$, 0.5M NaCl, pH 8.3) was added to the agarose and shaken for 2 hours at room temperature. The agarose was then washed, unreacted sites blocked by treatment with 1M ethanolamine, pH 8.0, for 4 hours, the agarose washed again and stored in PBS-N$_3$. The binding capacity of the antibody-agarose matrix was determined to be 10 µg BBI/ml matrix.

Figure 6:
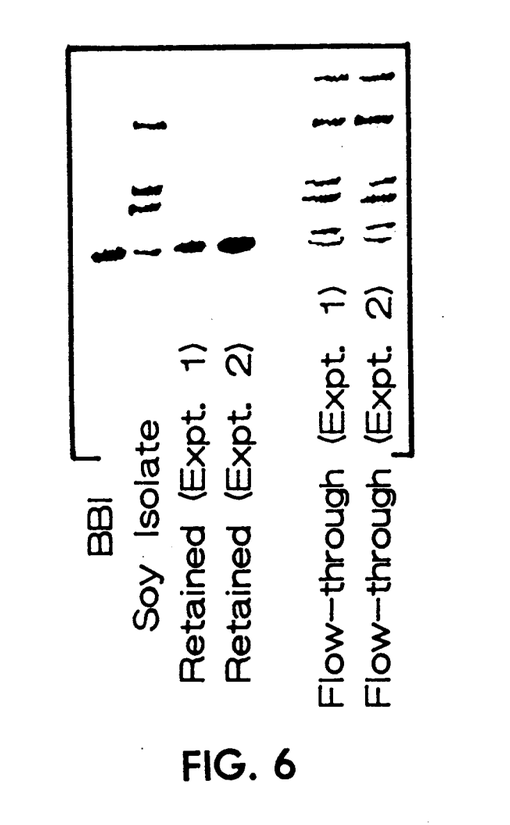
FIG. 6 shows gel electrophoretic analysis of purified BBI, an isolate from soy meal, and the retained and flow-through fractions from two affinity chromatography experiments using agarose coupled to monoclonal antibody to BBI.

Affinity purification of BBI from soy isolate. Soybeans from the Williams cultivar were ground in a Wiley mill and passed through a 40 mesh sieve. The meal was extracted with buffer and fractionated by ammonium sulfate precipitation and gel filtration on Sephadex G-100 (Pharmacia, Inc.) as described by D. L.-R. Hwang et al., 1977, supra, but without the addition of mercaptoethanol to the buffers. One ml of the resulting isolate was applied to a column containing 3.5 ml of the agarose matrix and allowed to bind for 20 min. The column was then eluted with PBS and the flow-through was collected. Retained proteins were then eluted with 0.1M acetic acid. Column fractions were dialyzed against water, lyophilized, redissolved in 0.1 to 0.2 ml PBS, and analyzed by electrophoresis in a polyacrylamide gel (12% acrylamide, 0.3% methylene bisacrylamide, 0.4M Tris-Cl, pH 8.8, containing 4M urea). FIG. 6 illustrates the electrophoretic results from two separate experiments, following staining with amido black. The retained fractions have one band with the mobility and antigenicity of native BBI.

EXAMPLE 4

Figure 7:
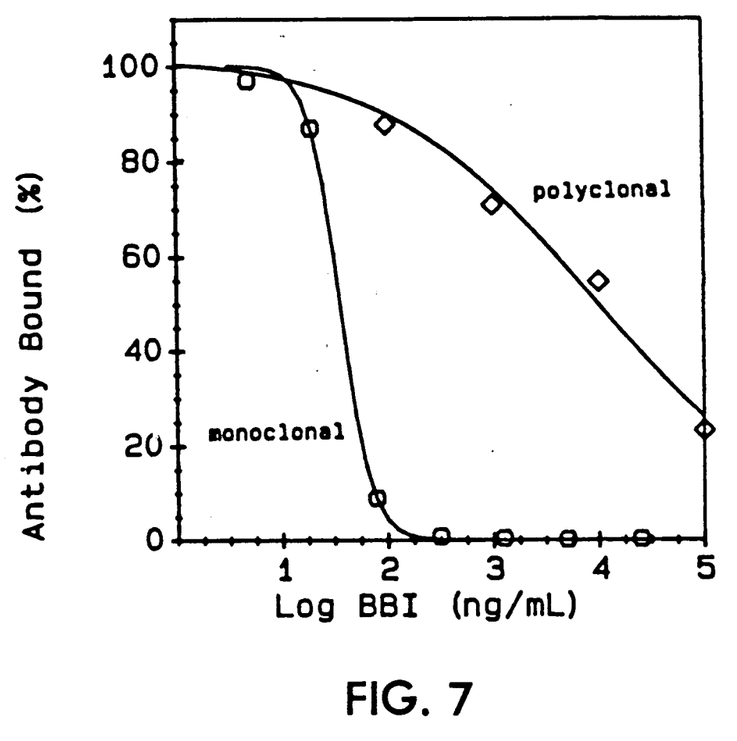
FIG. 7 shows ELISA standard curves for BBI using polyclonal antibody or monoclonal antibody of the invention.

Comparison of Affinity of Monoclonal Antibodies and Polyclonal Antibodies to BBI. Antisera were prepared from blood drawn one week after two intraperitoneal inoculations of BALB/c mice with 50 µg of classical BBI emulsified with complete Freund's adjuvant, as described in Example 1. The resulting polyclonal antibody preparation was compared to monoclonal antibody from ATCC HB 9657 by inhibition ELISA, as described in Example 1. The ELISA results are illustrated in FIG. 7. The monoclonal antibody of the invention produced a standard curve indicative of 100-fold higher sensitivity than the polyclonal antibody.

It is understood that the foregoing detailed description is given merely by way of illustration and that modification and variations may be made therein without departing from the spirit and scope of the invention.

Having thus described our invention, we claim:

1. A continuous hybrid cell line (ATCC No. HB 9657) which produces and secretes monoclonal antibodies which bind native Bowman-Birk inhibitor (BBI) with an affinity constant of at least $8 \times 10^7 M^{-1}$ and do not bind denatured BBI.

2. The continuous hybrid cell line described in claim 1 wherein said monoclonal antibodies do not bind with Kunitz trypsin inhibitor (KTI).

3. The continuous hybrid cell line described in claim 1 wherein said monoclonal antibodies are selective for an individual BBI.

4. The continuous hybrid cell line described in claim 1 wherein said monoclonal antibodies bind BBI which is bound to a protein at its chymotrypsin reactive site.

5. The continuous hybrid cell line described in claim 1 obtained using an immunization preparation comprising BBI which has not been treated with a crosslinking agent.

6. The continuous hybrid cell line of claim 1 which produces and secretes high affinity monoclonal antibodies to soybean BBI which do not bind with KTI, denatured BBI, or lima bean inhibitor (LBI).

7. Monoclonal antibody produced by hybridoma cell line ATCC No. HB 9657 which binds native BBI with an affinity constant of at least $8 \times 10^7 M^{-1}$ and does not bind denatured BBI.

8. The monoclonal antibody of claim 7 which does not bind with KTI.

9. The monoclonal antibody of claim 7 which is selective for an individual BBI.

10. The monoclonal antibody of claim 7 which binds BBI which is bound to a protein at its chymotrypsin reactive site.

11. Monoclonal antibody of claim 7 which does not bind with KTI, denatured BBI, or LBI.

12. A method for determining the amount of native BBI in a sample, which comprises:
    (a) incubating a sample with a monoclonal antibody produced by hybridoma cell line ATCC No. HB 9657 which binds native BBI with an affinity constant of at least $8 \times 10^7 M^{-1}$ and does not bind denatured BBI to obtain a mixture containing monoclonal antibody bound to native BBI in said sample and unbound antibody;
(b) contacting said mixture with a BBI-coated solid phase to bind said unbound antibody;
(c) separating said solid phase-bound antibody from said contacted mixture;
(d) detecting said separated solid phase-bound monoclonal antibody with labeled antibody; and
(e) determining the amount of native BBI in said sample by comparing the amount of detected labeled antibody to a standard curve.

13. A method for determining the amount of native BBI in a sample, which comprises:
(a) incubating a sample with labeled BBI to obtain a mixture;
(b) contacting said mixture with a solid phase coated with monoclonal antibody produced by hybridoma cell line ATCC No. HB 9657 which binds native BBI with an affinity constant of at least $8 \times 10^7 M^{-1}$ and does not bind denatured BBI to bind native BBI in said sample in said mixture and labeled BBI in said mixture;
(c) separating said solid phase-bound labeled BBI from said contacted mixture;
(d) detecting said separated solid phase-bound labeled BBI; and
(e) determining the amount of native BBI in said sample by comparing the amount of detected labeled BBI to a standard curve.

14. The method of claim 12 wherein said sample is selected from the group consisting of plant, animal or human tissue or fluid, a plant seed, a substance containing the product of a gene derived from a plant, and a foodstuff.

15. The method of claim 13 wherein said sample is selected from the group consisting of plant, animal or human tissue or fluid, a plant seed, a substance containing the product of a gene derived from a plant, and a foodstuff or plant tissue.

16. A method for attaching BBI to a solid phase, which comprises:
(a) attaching a monoclonal antibody produced by hybridoma cell line ATCC No. HB 9657 which binds native BBI with an affinity constant of at least $8 \times 10^7 M^{-1}$ and does not bind denatured BBI, to a solid phase by a covalent or noncovalent bond; and
(b) contacting said solid phase with BBI to form solid phase-bound BBI.

17. A kit useful for the detection of native BBI in a sample, which comprises a carrier being compartmentalized to receive one or more containers in close confinement therein; a first container means comprising a monoclonal antibody produced by hybridoma cell line ATCC No. HB 9657 which binds native BBI with an affinity constant of at least $8 \times 10^7 M^{-1}$ and does not bind denatured BBI; and a second container means comprising detection means selected from the group consisting of labeled BBI, labeled monoclonal antibody specific for BBI, and labeled immunoglobulin which binds to monoclonal antibody specific for BBI.

* * * * *